United States Patent [19]

Izumori et al.

[11] Patent Number: 4,923,803
[45] Date of Patent: May 8, 1990

[54] METHOD FOR DETERMINING GALACTITOL

[75] Inventors: Ken Izumori, Kagawa; Shuzo Sakai, Okayama, both of Japan

[73] Assignee: Kabushiki Kaisha Hayashibara Seibutsu Kagaku Kenkyujo, Okayama, Japan

[21] Appl. No.: 230,010

[22] Filed: Aug. 8, 1988

Related U.S. Application Data

[63] Continuation of Ser. No. 873,366, Jun. 12, 1986, abandoned.

[30] Foreign Application Priority Data

Jul. 3, 1985 [JP] Japan .................. 60-144585

[51] Int. Cl.$^5$ ............................................. C12Q 1/32
[52] U.S. Cl. ........................................ 435/26; 435/29; 435/104; 435/830
[58] Field of Search ...................... 435/4, 104, 14, 29, 435/26, 830

[56] References Cited

PUBLICATIONS

Izumori, K. et al., Applied and Environmental Microbiology, 46(5), 1055–1057 (1984).

Feigl, F., "Chemistry of Specific, Selective and Sensitive Reactions", p. 86, Academic Press, New York, 1949.

White, A. et al., "Principles of Biochemistry", p. 28, McGraw-Hill, New York, 1968 (Fourth Edition).

Primary Examiner—Christine M. Nucker
Assistant Examiner—Karen I. Krupen
Attorney, Agent, or Firm—Browdy and Neimark

[57] ABSTRACT

The galactitol level in the body fluid, e.g. blood or urine, is determined by the method that comprises allowing a body fluid sample to contact in vitro with a bacterium capable of producing D-tagatose from galactitol, and measuring the D-tagatose. Such bacterium is of the genus Arthrobacter, specifically, *Arthrobacter globiformis* ST-48 FERM P-7592 or its mutant, or of the genus Pseudomonas. The method is useful for detecting galactose dysbolism.

8 Claims, 2 Drawing Sheets

METHOD FOR DETERMINING GALACTITOL

This application is a continuation of patent copending application Ser. No. 873,366, filed June 12, 1986, now abandoned.

FIELD OF THE INVENTION

The present invention relates to a method to determine galactitol (or dulcitol), in particular, to a method to determine galactitol that comprises allowing a body fluid to contact in vitro with a bacterium capable of producing D-tagatose from galactitol, and measuring the resultant D-tagatose.

BACKGROUND OF THE INVENTION

It is known that D-galactose is converted in vitro into D-glucose-1-phosphate by the enzyme system including galactokinase (EC 2.7.1.6) and galactose-1-phosphate transferase (EC 2.7.7.10), and utilized.

In a dysbolism wherein the enzyme system is hereditarily deficient, the D-galactose accumulated in the body is reduced by aldose reductase (EC 1.1.1.21) into galactitol which is present in body fluids such as blood, urine, etc.

It is known that galactitol, accumulated in a large quantity in the body, crystallizes in the lens and becomes one of the major factors of cataract.

For this reason, galactitol in the body fluid, such as blood and ruine, should be qualitatively and quantitatively determined for prevention and diagnosis of cataract.

The methods which are generally employed to determine galactitol are those for polyols as reported, for example, in J. S. Dixon et al., *Analytical Chemistry*, Vol.26, pp.1092–1093 (1954), wherein polyols are oxidized with periodate and the reaction product is developed and then subjected to colorimetry. The method determines polyol in total but does not give the levels of particular polyols. In addition, the data obtained with the methods must be compensated because reducing substances such as glucose tend to interfere the methods.

Galactitol is also determinable by gas-chromatography. Gas-chromatography of galactitol, however, has the drawback of unfavorably requiring, in addition to complicated pretreatments such as trimethylsilylation, a high experimental skill to allow fractional determination of other polyols such as D-mannitol, D-sorbitol, etc.

SUMMARY OF THE INVENTION

In view of the foregoing, one object of the present invention is to provide a method to determine the galactitol in the body fluid.

Still another object of the present invention is to reduce the drawback of the known methods.

These and other objects as may become apparent hereinafter have been attained by the method that comprises allowing a body fluid to contact in vitro with a bacterium capable of producing D-tagatose from galactitol to convert the galactitol in the body fluid into D-tagatose, and measuring the D-tagatose.

BRIEF DESCRIPTION OF THE ACCOMPANYING DRAWINGS

DESCRIPTION OF THE PREFERRED EMBODIMENTS

Figure 1:
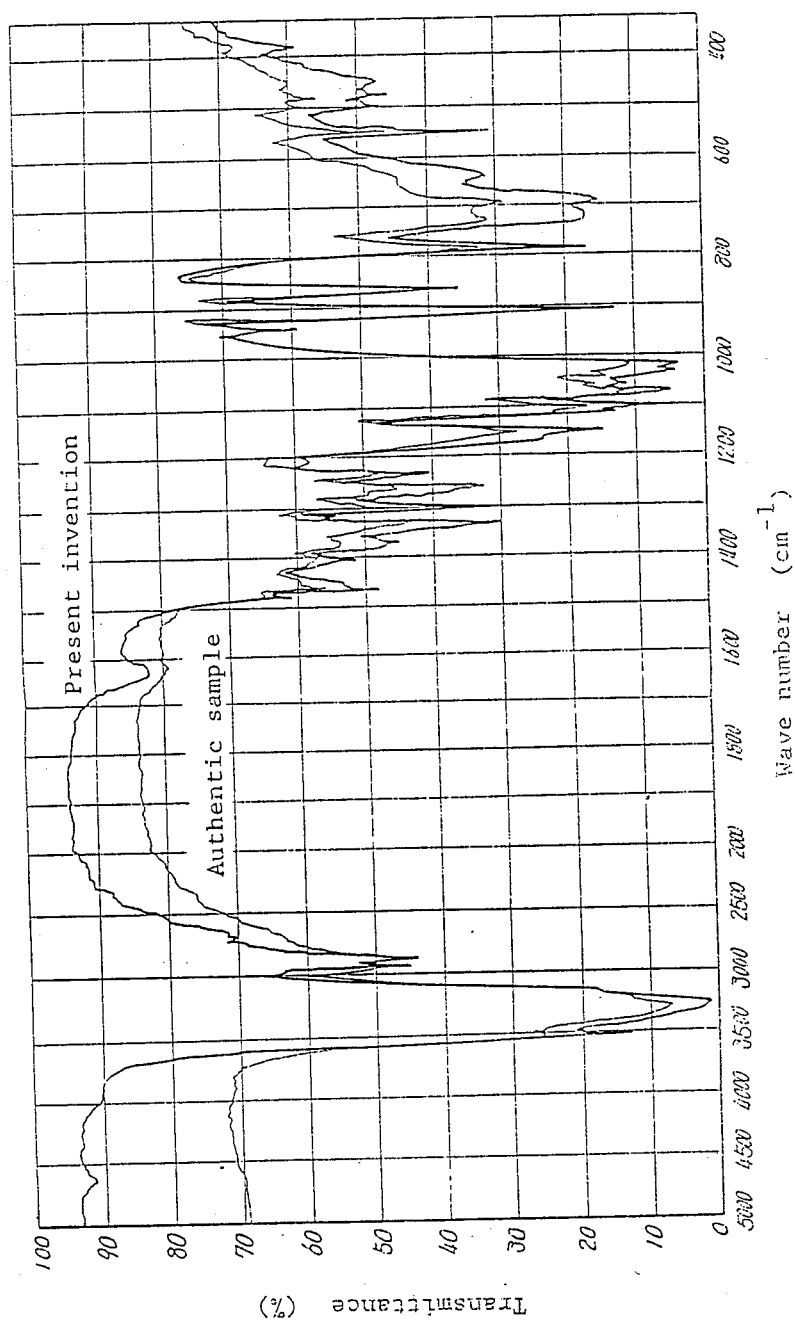
FIG. 1 shows the infrared absorption spectra of an authentic D-tagatose sample and a crystalline D-tagatose obtained according to the invention.

The bacteria advantageously usable in the invention are those which are of the genus *Pseudomonas*, for example, as reported in *Biochemical Journal*, Vol.64, pp.394–405 (1956), and of the genus *Arthrobacter*, for example, as reported by the present inventors in *Applied and Environmental Microbiology*, Vol.46, pp.1055–1057 (1984).

Specifically suited bacteria are *Arthrobacter globiformis* ST-48 and its mutants which have a high ability of converting galactitol into D-tagatose.

*Arthrobacter globiformis* ST-48 has been deposited since May 1, 1984 at the Fermentation Research Institute, Agency of Industrial Science and Technology, Ministry of International Trade and Industry, 1-3, Higashi, 1 chome, Yatabe-machi, Tsukuba-gun, Ibaraki-ken, Japan, under the accession number of FERM P-7592.

The bacteriological properties of *Arthrobacter globiformis* ST-48 will hereinafter be described.

A. Source and station
   Isolated from a soil in Tsuyama-shi, Okayama-ken, Japan
B. Morphology
   (1) Shape and size
      Rod-shaped or, fewer, spherical or oval: 0.6–0.8 microns×1.0–2.0 microns
   (2) Polymorphism
      A few curved cells
   (3) Motility
      None
   (4) Flagelum
      None
   (5) Spore
      None
   (6) Gram-stain
      Negative
   (7) Capsule
      None
   (8) Acid-fast stain
      Negative
C. Growth on culture medium
   (1) Bouillon agar plate (at 28° C. for 5 days)
      Growth of the cell was relatively slow, and colonies were formed after a lapse of 5 days. The colonies had a smooth but convex, spherical, end-rounded surface with a glistening, whitish yellow appearance, and the content of the colonies was translucent and homogeneous. No pigment was formed.
   (2) Bouillon slant (at 28° C. for 5 days)
      Growth of the cell was relatively slow or moderate. The colonies had a filamentous, smooth, flatly-convex surface with a translucent, grey, glistening appearance. The culture was relatively viscous, but no pigment was formed.
   (3) Bouillon liquid culture medium (at 28° C. for 3 days)

Growth of the cell was relatively slow, and the culture wholly became slightly turbid as the cultivation proceeded. The cell grew in a thick membranous form on the surface of the culture resulting in sediment formation. Neither pigment nor gas was formed.

(4) Bouillon stab culture (at 28° C. for 5 days)

Colonies were formed on the surface of the culture medium, while growth in spiniform was noted at the upper layer of the stab lines. Neither gas nor pigment was formed.

(5) Bouillon gelatine stab culture
  (i) Growth at 20° C. for 40 days: Colonies were formed on the surface of the culture medium around its stabbed points, while at the upper layer was noted a growth in spiniform, but liquefaction.
  (ii) Growth at 28° C. for 40 days: The cell grew over the culture medium. Cultivation after cooling of the culture medium solidified its gelatinous component.

(6) Litmus and milk (at 28° C. for 40 days)

Litmus did not change, while bromocresol purple turned to blue indicating that the culture medium was alkalified. Neither liquefaction nor aggregation was noted.

D. Physiological properties (1) Reduction of nitrate
    Positive
(2) Denitrification reaction
    Positive
(3) MR test
    Negative
(4) VP test
    Negative
(5) Formation of indole
    Negative
(6) Formation of hydrogen sulfide
    Positive
(7) Hydrolysis of starch
    Positive but very weak
(8) Utilization of citric acid
    Positive
(9) Utilization of inorganic nitrogen
    Utilizing sulfate and ammonium salt
(10) Formation of pigment
    Not formed
(11) Urease
    Positive
(12) Oxidase
    Positive
(13) Catalase
    Positive
(14) Growth ranges
    pH, from 5 to 8; temperature, from 5° to 37° C.; saline, up to 3%
(15) Behavior to oxygen
    Aerobic
(16) O-F test
    Scarcely degraded saccharide (glucose)
(17) Formation of acid or gas from saccharide

|  | Acid | Gas |
| --- | --- | --- |
| L-Arabinose | + | − |
| D-Xylose | + | − |
| D-Glucose | − | − |
| D-Fructose | − | − |

-continued

|  | Acid | Gas |
| --- | --- | --- |
| Sucrose | − | − |
| Lactose | − | − |
| Mannitol | − | − |
| Glycerol | − | − |

(18) Growth pH
    pH 7.62 when cultured with proteose-peptone-glucose medium
(19) Degradation of cellulose
    Negative
(20) Heat-resistance
    No growth after 10 minutes-heating at 80° C.
(21) Nutritive requirement
    None With reference to *Bergy's Manual of Determinative Bacteriology*, 7th edition (1957), and ibid., 8th edition (1974), this cell strain was grouped into the genus *Arthrobacter* based on the evidences that the cell strain was a rod-shaped, gram-negative, aerobic bacterium; that the cell strain did not form spore; that the cell strain was non-motile, catalase-positive, oxidase-positive, and slightly polymorphic; and still that the cell strain was isolated from soil. In detail, the cell strain formed a small amount of acid from saccharides, reduced nitrate, did not form indole, and utilized nitrate and ammonium salt as the nitrogen source. Based on the additional properties that the cell strain utilized citric acid without forming pigment; that the cell strain grew even at 37° C.: and that the cell strain weakly degraded starch, the cell strain was identified to be a bacterium of the species *Arthrobacter globiformis*, and then designated as "*Arthrobacter globiformis* ST-48".

The bacteria that can be advantageously used in the invention are those which has the possible highest ability of converting galactitol into D-tagatose, and which can be prepared by cultivation under aerobic conditions with a nutrient culture medium containing as the carbon source, generally, sugar alcohol(s), such as galactitol, sorbitol, etc.

For example, a frozen-thawed-, lyophilized- or immobilized bacterium preparation can be advantageously used in the invention as long as the preparation is capable of converting galactitol into D-tagatose, and the bacteria should not be restricted to intact preparations.

An immobilized bacterium in beads or sheet prepared, for example, by treatment of an intact bacterium cell with a diisocyanate compound such as toluene 2,4-diisocyanate, or a dialdehyde compound such as glutaraldehyde under slightly acidic or neutral conditions; by entrapment inside a hollow fiber of a semipermeable membrane: or by encapsulation of an intact bacterium cell with agar, gelatine, κ-carrageenan or arginate can be advantageously used in a repeated manner.

The wording "body fluid" shall mean body fluids, such as blood or urine, derived from human or non-human warm-blooded animal.

The step of allowing a body fluid to contact in vitro with a bacterium capable of producing D-tagatose from galactitol can be carried out, for example, by placing a body fluid sample intact or after treatment, such as centrifugation, protein removal or dialysis, in an appropriate vessel such as microwell, porcelain well, test tube or flask; adding a bacterium capable of producing D-tagatose from galactitol to the vessel; and incubating the mixture, generally, at about 10° to 50° C. for about 0.1 to 100 hours under aeration conditions so as to satisfactorily effect conversion of the galactitol into D-tagatose.

The method for qualitative or quantitative determination of the resultant D-tagatose can be freely chosen.

Such method may be a chemical method such as Fehling's or cysteine-carbazole method wherein the reducing property of D-tagatose or its properties as ketose are utilized respectively; or a biochemical method wherein the specific reaction of D-tagatose with galactitol dehydrogenase (EC 1.1.1.16) is utilized: that is, the amount of D-tagatose is proportional to the decreased amount of $NADH_2$ as photometrically measured at 340 nm.

The galactitol in the body fluid can be easily determined by measuring D-tagatose in this way because in the present method the galactitol is converted into D-tagatose in a high yield.

The present invention can be advantageously used in detection of galactose dysbolism, as well as in their prevention and diagnosis.

The present invention will be further explained with the following Experiments.

EXPERIMENT 1

One hundred milliliter aliquots of a liquid culture medium consisting of 0.2 w/v ammonium sulfate, 0.24 w/v % dipotassium phosphate, 0.01 w/v % magnesium sulfate heptahydrate, 0.5 w/v % yeast extract, 2 w/v % galactitol and deionized water were placed in 20 shaking flasks, capacity of 500 ml, autoclaved at 120° C. for 20 minutes, inoculated with a platinum loop of a seed culture of *Arthrobacter globiformis* ST-48 FERM P-7592, and subjected to shaking culture 30° C. for 7 days.

Gas-chromatography of the culture broth revealed no galactitol, and the D-galactose yield was about 85% based on the material galactitol. The culture broth was then centrifuged into the cell and supernatant.

The supernatant was adjusted to pH 7.6 by addition of 0.1 volume of 25 w/v % zinc sulfate, followed by centrifugation. Thereafter, the newly formed supernatant was decolored with activated carbon, deionized with "Diaion SK1B (H-form)", an anion exchange resin and "Diaion WA30 (OH-form)", a cation exchange resin, both commercialized by Mitsubishi Chemical Industries Ltd., Tokyo, Japan, and concentrated in vacuo to obtain a transparent syrup with a concentration of about 95%. The syrup was admixed with three volumes of anhydrous methanol, and then allowed to stand at ambient temperature to effect crystallization. The resultant crystal was filtered, washed with anhydrous methanol, dissolved in minimum water, added with three volumes of anhydrous methanol, recrystallized, filtered, washed and recovered.

The yield of the crystal was about 70% based on the galactitol.

In order to identify the crystal thus obtained, the physicochemical properties of the crystal were compared with those of an authentic D-tagatose sample purchased from Sigma Chemical Co., MO, USA.

(1) Paper-chromatography

The crystal and authentic D-tagatose sample were spotted on the same "Filter Paper No.50", a product of Toyo Roshi KK, Tokyo, Japan, developed in ascending manner with either Solvent I, a mixture of n-butanol, acetic acid and water (12:3:5), or Solvent II, a mixture of ethyl acetate, pyridine and water (12:5:4), and developed with alkaline silver nitrate, followed by comparison of $R_f$ values.

|  | $R_f$ value | |
|---|---|---|
|  | Solvent I | Solvent II |
| Authentic sample | 0.72 | 0.84 |
| Present invention | 0.73 | 0.85 |

(2) Melting point

The authentic sample showed a melting point of 130°–131° C.; the crystal according to the invention, 131°–132° C.; and the mixture thereof, 130°–131° C.

(3) Specific rotatory power $[\alpha]_D^{20}(C=10\%$ in $H_2O)$

The specific rotatory power of the authentic sample was minus 5.10 degrees: and that of the crystal according to the invention, minus 4.98 degrees (4) Infrared absorption spectrum The infrared absorption spectra of the crystal and authentic sample using the KBr tablet method were as shown in FIG. 1. As evident from FIG. 1, the infrared absorption spectrum of the crystal was in good agreement with that of the authentic sample.

These data confirmed that the crystal obtained by the present method was crystalline D-tagatose.

EXPERIMENT 2

EXPERIMENT 2-(1)

Preparation of immobilized bacterium

A bacterium cell, obtained by the method in Experiment 1, was washed with 0.05M phosphate buffer (pH 7.0), collected by centrifugation, and suspended in water to prepare a suspension containing 1 g wet cell per ml.

κ-Carrageenan, 0.4 g, was dissolved in 12 ml of 0.6% aqueous sodium chloride solution by heating, kept at 45° C., admixed with 2 ml of the cell suspension, and solidified by cooling.

The resultant product was cut, shaped and stored in 0.3M aqueous potassium chloride solution.

EXPERIMENT 2-(2)

Conversion into D-tagatose by immobilized bacterium

One hundred milliliter aliquots of a liquid culture medium having the same formula as in Experiment 1, except that 0.5 w/v % yeast extract and 2 w/v % galactitol were replaced respectively with 0.1 w/v yeast extract and 0.5 w/v D-sorbitol, were placed in shaking flasks, autoclaved similarly as in Experiment 1, added respectively with the immobilized bacterium prepared in Experiment 1-(2), and shaken at 30° C. for 12 hours, followed by filtration.

The ability to convert galactitol into D-tagatose of the obtained immobilized bacterium was improved per piece by about 8- to 10-folds in comparison with that of the immobilized bacterium in Experiment 2-(1).

EXPERIMENT 2-(3)

Quantitative determination of galactitol

A half milliliter of a sample liquid containing 0.5 ml of 0.05M phosphate buffer (pH 7.0) and 0 to 100 micrograms of galactitol/ml, and a piece of the immobilized bacterium (0.06 g) prepared in Experiment 2-(2) were placed in a test tube, and shaken at 35° C. for 1 hour. Thereafter, the immobilized bacterium was removed from the reaction mixture, and the residual liquid, as the D-tagatose solution, was added per ml with 0.2 ml of 1.5 w/v % aqueous cysteine hydrochloride solution, 6 ml of 70 w/v % cysteine sulfate solution, and 0.2 ml of 0.12 w/v % methanolic carbazole solution in accordance with the cysteine-carbazole method as reported in *Journal of Biological Chemistry*, Vol.192, pp.583–587 (1951). Thereafter, the mixture solution was developed at 50° C. for 30 minutes, and measured for the absorbance at 580 nm using 1 cm cuvette. The results were as shown in FIG. 2.

Figure 2:
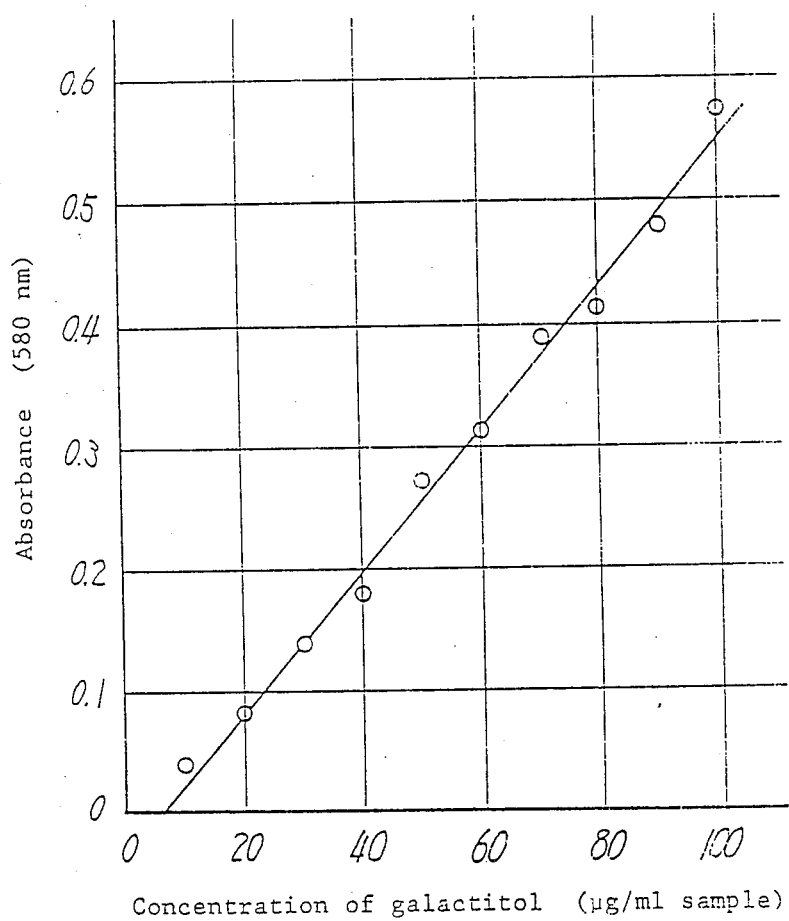
FIG. 2 is illustrative of the correlation between concentration of galactitol and absorbance.

Since as evident from FIG. 2 the concentration of galactitol was, in the range of 20–100 micrograms, in good correlation with the absorbance, this method can be satisfactorily used as trace analysis of galactitol.

EXPERIMENT 2-(4)

Effect of other saccharide on determination of galactitol

The effects of other saccharides on determination of galactitol were tested.

As other saccharide, D-glucose, D-galactose, D-mannose, D-fructose, D-mannitol, D-sorbitol, D-arabitol, L-arabitol, xylitol, ribitol, myo-inositol, maltitol, lactitol, maltose, lactose and sucrose were used.

An aqueous solution containing 50 micrograms of galactitol and 50 micrograms of either saccharide per ml was used as the sample liquid. An aqueous solution containing only 50 micrograms of galactitol per ml was used as the control liquid.

Galactitol was determined similarly as in Experiment 2-(3).

The obtained data were in good agreement with that of the control, and no interference by other saccharide was noted.

Several embodiments according to the invention will hereinafter be described.

EXAMPLE 1

Qualitative method

One milliliter of urine was collected respectively from one healthy person and two galactose dysbolism persons, followed by dialysis using multidialyzer cells. The liquids outside the cell were placed in white porcelain wells, added respectively with 0.1 ml of a cell suspension, prepared by the method in Experiment 1-(1) and diluted 50-time dilution with water, reacted at 35° C. for 1 hour, and then developed by addition of the cysteine-carbazole reagent.

As the result, the reaction mixture derived from each galactose dysbolism person's urine developed reddish purple much stronger than that derived from the healthy person.

This method can be advantageously used to detect galactose dysbolism because the D-tagatose derived from galactitol can be qualitatively determined by the method.

EXAMPLE 2

Quantitative method

One milliliter of urine was collected respectively from one healthy person and two galactose dysbolism persons, and dialyzed similarly as in Example 1, thereafter, the liquids outside the multidialyzer cells were determined for galactitol in accordance with the method in Experiment 2-(3).

As the result, the galactose dysbolism persons' urines contained respectively 140 micrograms or 220 micrograms of galactitol per ml, while no galactitol was detected in the healthy person's urine.

This method can be advantageously used to detect galactose dysbolism, as well as method to determine urinary galactitol in galactose loading test.

EXAMPLE 3

Quantitative method

Serum specimens obtained by heparinization and subsequent centrifugation of blood specimens collected respectively from two healthy persons and two galactose dysbolism persons were dialyzed similarly as in Example 1, and the liquids outside the multidialyzer cells were determined for galactitol in accordance with the method in Experiment 2-(3).

As the result, no galactitol was detected in the healthy persons' sera, while the galactose dysbolism patients' sera contained 100 micrograms and 180 micrograms of galactitol per ml respectively.

This method can be advantageously used as the method to detect galactose dysbolism, as well as the method to determine urinary galactitol in galactose loading test.

As described above, qualitative or quantitative determination of the galactitol in the body fluid which has been deemed very difficult can be easily and specifically carried out by the present invention without interference by other saccharides.

Thus, the present invention is useful as the test method to detect galactose dysbolism which is characterized by the presence of galactitol in the body fluid, as well as the prophylactic or diagnostical method for galactose dysbolism.

Having described specific embodiments of our bearing, it is believed obvious to those skilled in the art that various modifications and variations of our invention are possible in light of the above teaching.

We claim:

1. A clinical assay method for indicating the probability of human developing a cataract or for indicating the possible presence of human cataract, comprising:
   providing body fluid from said human containing galactitol in an amount up to about 220 micrograms/ml;
   incubating the body fluid together with a bacterium capable of converting the galactitol in the body fluid into D-tagatose; and
   determining the amount of the resultant D-tagatose; whereby the determination of a galactitol level over a predetermined amount is indicative of the probability of developing a human cataract or is indicative of the possible presence of a human cataract.

2. The assay in accordance with claim 1, wherein said bacterium is of the genus Arthrobacter.

3. The assay in accordance with claim 1, wherein said bacterium is of the genus Pseudomonas.

4. The assay in accordance with claim 1, wherein said bacterium is *Arthrobacter globiformis* ST-48 FERM P-7592.

5. The assay in accordance with claim 1, wherein said galactitol is quantitatively determined.

6. The assay in accordance with claim 1, wherein said galactitol is qualitatively determined.

7. The assay in accordance with claim 1, wherein said bacterium is immobilized.

8. A clinical assay method for indicating the probability of a human developing a cataract or for indicating the possible presence of human cataract, comprising:

providing body fluid from said human containing galactitol and formulating a sample such that the galactitol is present in an amount in the range of 20–100 micrograms/ml;

incubating the body fluid together with a bacterium capable of quantitatively converting the galactitol in the sample into D-tagatose; and determining the amount of the resultant D-tagatose;

whereby the determination of a galactitol level over a predetermined amount is indicative of the probability of developing a human cataract or is indicative of the possible presence of a human cataract.

* * * * *